United States Patent [19]

Honnen

[11] 4,418,222

[45] Nov. 29, 1983

[54] CONTINUOUS PHENOL ALKYLATION PROCESS

[75] Inventor: Lewis R. Honnen, Petaluma, Calif.

[73] Assignee: Chevron Research Company, San Francisco, Calif.

[21] Appl. No.: 267,164

[22] Filed: May 26, 1981

[51] Int. Cl.³ .................... C07C 37/14; C07C 39/06
[52] U.S. Cl. ................................. 568/793; 568/790; 568/788
[58] Field of Search .................. 568/793, 790, 788

[56] References Cited

U.S. PATENT DOCUMENTS

| | | | |
|---|---|---|---|
| 2,008,017 | 7/1935 | Hester | 568/793 |
| 3,932,537 | 1/1976 | Wetzel et al. | 568/788 |
| 4,198,531 | 4/1980 | Merger et al. | 568/793 |
| 4,228,311 | 10/1980 | Dodd | 568/788 |
| 4,236,033 | 11/1980 | Alfs et al. | 568/793 |

Primary Examiner—Werren B. Lone
Attorney, Agent, or Firm—D. A. Newell; J. M. Whitney; V. J. Cavalieri

[57] ABSTRACT

A continuous process is provided for the production of para alkyl phenols. In the process a mixture of phenol, olefin and strong organic acid, is reacted for a brief period of time. The resulting reaction mixture is quenched, and the para alkyl phenol recovered.

3 Claims, 1 Drawing Figure

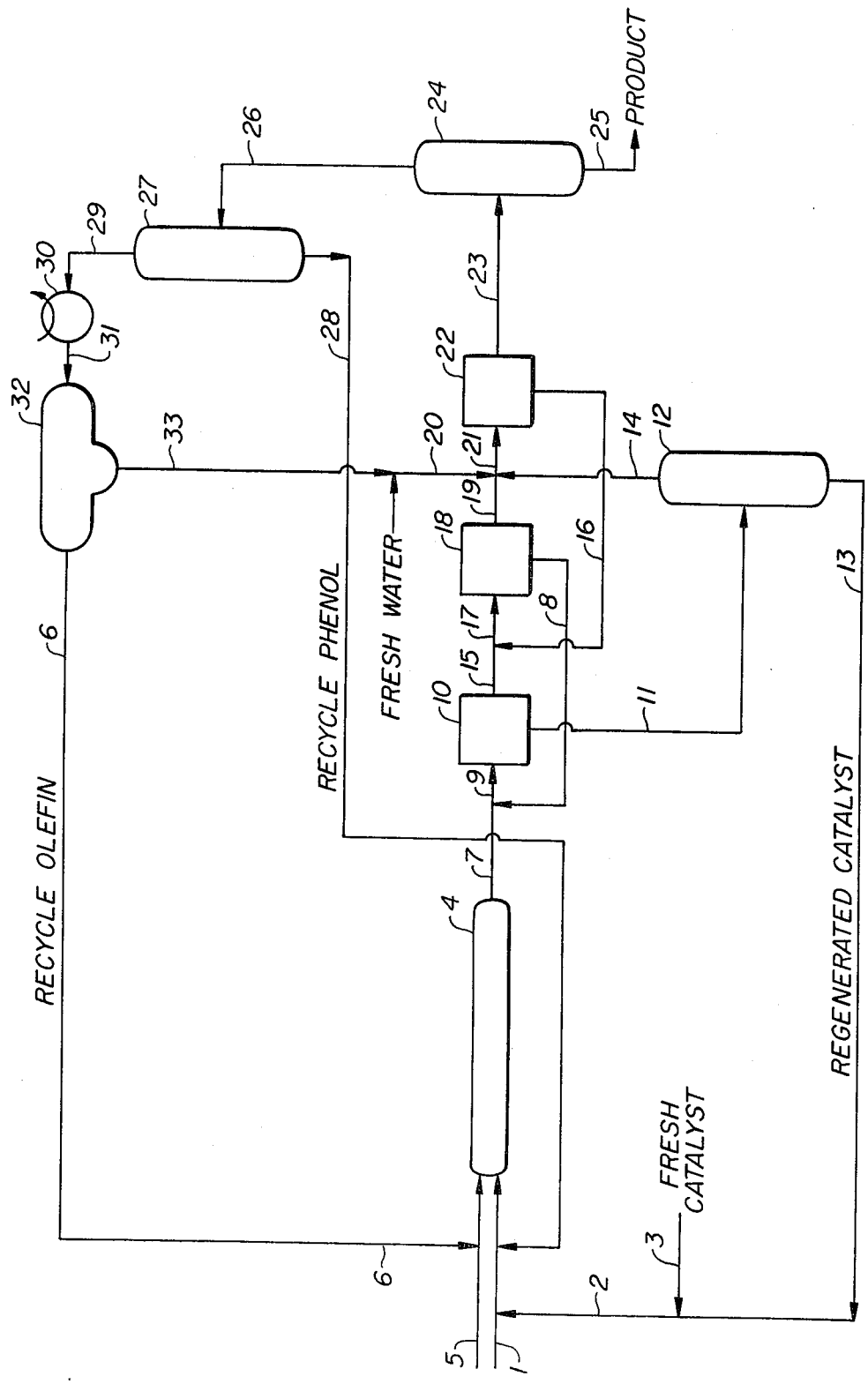

CONTINUOUS PHENOL ALKYLATION PROCESS

BACKGROUND OF THE INVENTION

This invention relates to an improved process for the production of para alkyl phenol. It particularly relates to an improved continuous process for the production of para alkyl phenol in which the alkyl group is derived from a low molecular weight polypropylene.

In conventional processes for preparing alkyl phenols, phenol is alkylated with a source of an alkyl group, usually an olefinic hydrocarbon, for example a polyolefin, in the presence of an alkylation catalyst. It is known that, in general, strong acid catalyzed phenol alkylation is selective and that para alkyl phenol is initially formed. Rearrangement to the ortho isomer, however, is a facile concurrent or subsequent reaction, especially where the alkylation agent is a labile group, such as a tertiary olefin, and the catalyst is a strong acid. For use as a lube oil additive, para monoalkyl phenols are, in general, superior to the corresponding ortho isomers, the latter exhibiting undesirable effects upon lube oil viscosities and the like. In order to avoid undesirable production of ortho alkyl phenol, it has been conventional to employ weak acid catalysts, acidic resins, and water moderated inorganic acids, as well as acidic clays and the like. The penalty in such is that long contact or reaction times (six to eight hours) are usually required. These long reaction periods are not satisfactory for continuous processing.

An object of this invention is to provide a continuous process for selectively producing para mono alkyl phenols in high yield and at a rapid rate. Other objects will be evident from the examples and description to follow.

SUMMARY OF THE INVENTION

An improved process is provided for the continuous production of para alkyl phenol. In the process phenol is reacted with a polyolefin under liquid phase alkylation conditions by contacting the reactants in the presence of an effective amount of at least one very strong hydrolytically stable protonic organic acid. The contacting of the reactants is effected at an initial temperature in the range of from about 20° C. to 150° C. for a period sufficient for substantial completion of the alkylation yet insufficient for appreciable isomerization of the para alkyl phenol, usually in the range 0.5 to 10, preferably 0.5 to 5 minutes. The alkylation reaction is quenched by intimate introduction of a polar solvent, preferably water, which introduction results in (1) formation of a polar liquid phase containing most, if not all, of the acid catalyst and (2) formation of an organic phase containing the para alkyl phenol. The para alkyl phenol is recovered by any convenient method, for example, fractional distillation for removal of nonpolar organic solvent, if used, and unconverted reactants.

In a further aspect of the invention, recovered acid catalyst and polar quench liquid are recycled to the process.

The term "tertiary olefin" is used herein in its conventional sense; that is, by a "tertiary olefin" is meant at least one of the carbon atoms of the carbon-carbon double bond pair is a tertiary carbon atom, e.g. is attached to three other carbon atoms.

EMBODIMENT

The FIGURE illustrates a schematic process flow diagram of a preferred embodiment of the invention wherein phenol is alkylated with propylene tetramer for the production of para dodecyl phenol for use as a lube oil additive or as a precursor thereof. The alkylation is preferably catalyzed by trifluoromethanesulfonic (TMS) acid.

A mixture of fresh and recycle phenol, containing about 1 part by weight of TMS acid per 100 parts of phenol, is introduced via lines 1, 2, 3 and 28 into line reactor 4. This reactor is a static mixer fitted with baffles or the like as required for rapid and efficient mixing of charged materials. A mixture of fresh and recycle propylene tetramer is introduced via lines 5 and 6 into reactor 4 at a rate which provides a phenol to tetramer mol ratio of about 1.8 to 1. The feed stock mixture is charged to the reactor at an initial temperature of 40° C. The total charge to reactor 4 is introduced at a rate which provides a reaction time (residence time in reactor 4 plus transit time in line 7) of about 2 minutes. During this time there is an exothermic reaction with substantially complete conversion of the tetramer to para polypropyl phenol. The reaction is then quenched by introducing water via line 8 into the advancing product stream in line 7, thereby producing an aqueous phase containing the TMS acid and an organic phase containing unreacted phenol, polypropyl phenol and a trace of propylene tetramer. These phases are separated by delivery of the quenched reaction mixture via line 9 to separator 10, the first of a series of three-phase separators which, together with associated water lines, make up the wash section of the process.

The acid-containing aqueous phase is withdrawn via line 11 from separator 10 and passed to acid regenerator column 12 for fractionation into a overhead water fraction and a bottoms TMS acid fraction. The acid and water, are withdrawn via lines 13 and 14 respectively from column 12 and recycled to the process.

The organic phase separated in 10 is withdrawn via line 15 and together with added wash water from line 16 is passed via line 17 to separator 18 wherein the second phase separation is carried out. The water phase is withdrawn from separator 18 via line 8 for use in quenching the reaction stream in line 7. The separated organic phase is withdrawn via line 19 and together with wash water from lines 14 and 20 is passed via line 21 to separator 22 wherein the third phase separation is carried out. The water phase is withdrawn from separator 22 via line 16 for use as upstream wash water.

The organic phase separated in 18 is withdrawn from separator 22 via line 23 and is passed to product stripper column 24 for fractionation into an overhead stream containing water, phenol and unconverted tetramer and a bottoms fraction which is the desired para polypropyl phenol. The product fraction is withdrawn from column 24 via line 25 and passed to storage.

The overhead fraction from column 24 is passed via line 26 to recycle-drier column 27 for fractionation into a dry phenol bottoms fraction and a water-tetramer overhead vapor fraction. Via line 28 the bottoms fraction is withdrawn from column 27 for recycle to the process. Via line 29 the overhead vapor fraction is withdrawn from column 27 and passed to in direct heat exchanger 30 where it is cooled and condensed and thereafter passed via line 31 to settler 32 wherein the condensed vapors are separated into a water phase and an olefinic hydrocarbon phase. Via lines 33 and 6, the hydrocarbon and water phases, respectively, are withdrawn from settler 32 and recycled to the process.

The above-described process provides for rapid para alkylation of phenol in high yields. The product contains little or no dialkyl phenol and, despite the strong acid catalyst used, a surprisingly small amount of ortho alkyl phenol is produced.

Olefin

Olefinic hydrocarbons, in general, having carbon atom contents in the range 3 to 60 are satisfactory feeds for the process of the invention and are contemplated for such use. This process is especially advantageous where the olefin is a tertiary olefin (see discussion supra). These olefins are labile in that they yield alkyl aromatic compounds, such as phenols and hydrocarbons, which isomerize readily, especially under strong acid catalysis conditions. Thus, while the initial alkylation using a tertiary olefin may yield a desired isomer, for example a para alkyl phenol, subsequent isomerization resulting under conventional alkylation conditions usually results in appreciable isomerization of the para alkyl phenol to the ortho isomer. Accordingly, preferred feeds herein are tertiary olefinic hydrocarbons including olefins obtained by the oligomerization of low molecular weight olefins, a typical one being polypropylene also known as propylene tetramer. Such olefins are usually obtained from the conventional polymerization of $C_3$ to $C_5$ olefins and mixtures thereof and of these olefins in admixture with a minor amount of ethylene. Representative polyolefins include polypropylenes, especially the trimer and tetramers of propylene, polybutenes, hexene dimer, heptene dimer, octene dimer and the like. Polypropylene tetramer which is a mixture of olefins prepared by polymerizing propylene and having an average of 12 carbon atoms is most preferred.

Acid Catalyst

Very strong protonic organic acids are satisfactory for use as catalysts in the process of the invention and are contemplated for such use. One can simply and easily determine the suitability of the organic acids by carrying out the following test:

In an insulated container (e.g. Dewar flask)
(1) Dissolve 15 grams of acid in 85 grams of phenol;
(2) Adjust to a temperature of 40° C.;
(3) Add rapidly (10 seconds), 56 grams of diisobutylene, also at 40° C.;
(4) Measure temperature rise;
(5) Satisfactory acids give a temperature increase greater than 25° C. in 5 minutes.

In addition, the acids must be hydrolytically stable, i.e., they must be stable in water. Preferably the strong organic acids are perfluoroalkane and perfluoroaryl-sulfonic or phosphonic acids and most preferably perfluoroalkane sulfonic acids. Representative organic acids suitable for use herein include:

Trifluorobenzenesulfonic acid
Trifluoromethanesulfonic Acid
Trifluoromethylphosphonic Acid
2,4,6-Trinitrobenzenesulfonic Acid
Trichloromethane sulfonic Acid In addition to the fast reaction rates provided by these strong organic acids, they are advantageous herein in that they are readily recoverable as a recyclable bottoms fraction, for example, by fractionally distilling off water. They are also readily extracted from an organic phenolic medium by a polar solvent, for example, water.

The amount of acid required for effective catalysis of the alkylation varies depending, in the main, upon acid strength. In general, based upon the sum of the weights of the acid and phenol, an effective amount is in the range of from about 0.5 to 25 percent, preferably 1 to 10 percent.

Reaction Time

Satisfactory reaction times for the present process vary depending upon several factors, including the strength of the acid catalyst, the temperature, and the particular olefin employed. In general, substantially complete conversion of the olefin to para alkyl phenol occurs with little or no concurrent or subsequent isomerization when reaction times are in the range of from about 0.5 to 10, preferably 1 to 5 minutes. The use of short reaction times are, of course, desirable in terms of efficient utilization of costly process reactors.

Temperature

A range of temperatures is satisfactory for use in the process of the invention. Temperatures of the feed stock are regulated to values within the range of 20° to 150° C., preferably 30° to 100° C. and more preferably 40° to 70° C. The exothermic heat of reaction raises the temperature within the reactor to a considerably higher value. In general, the higher temperatures require shorter reaction time.

Reactant Ratio

A prime objective of the process described herein is the production in high yield of para alkyl phenols. To this end, the production of dialkyl phenols must be minimized by the use of reactant mol ratios, i.e., phenol to olefin, favoring mono alkylation of phenol. Satisfactory ratios are, in general, in the range above about 1.5. Usually a moderate excess of phenol in the reaction system is desirable. On the other hand, as this excess becomes increasingly large, the efficiency of the process in terms of effective reactor utilization, fractionation costs and the like, diminishes. Preferably the phenol to olefin mol ratio is in the range of from about 5:1 to 1:1, and more preferably is about 2:1–3:1.

Solvent

An inert solvent or diluent, such as a saturated hydrocarbon mixture, may be advantageously used in the process herein, for example, to facilitate phase separations, reduce viscosity of reaction and product mixtures or the like. In general, however, it is preferred to avoid using a solvent in order to minimize processing costs.

The invention will be further understood by reference to the following example.

EXAMPLE

A 500 ml round bottom flask equipped with a stirrer, reflux condenser, and thermometer, was charged with 118.9 grams of a 1% trifluoromethane sulfonic acid in phenol solution. This solution was warmed to 100° C. Then 93.9 grams of propylene tetramer at 100° C. was added all at once through the inlet port. The temperature rose from 100° C. to 142° C. in 190 seconds.

After 2 minutes at 142° C., a 10 ml aliquot was removed and quenched in caustic and extracted with toluene. This extract was rapidly evaporated to dryness by blowing a stream of nitrogen over a thin film of it at about 90° C.

Infrared analysis showed a 4% ortho content. A gas chromatography analysis showed practically no dialkyl benzene; and only a very small amount of unreacted tetramer. These results show better than 90% yield of a monopara alkyl phenol obtained using the process of this invention.

What is claimed is:

1. An improved process for the continuous production of para monoalkyl phenol comprising reacting phenol with polypropylene under liquid phase alkylation conditions by contacting the reactants in the presence of an effective amount of trifluormethanesulfonic acid catalyst, said contacting being at a temperature in the range of from about 20° C. to 150° C. for a period of from 0.5 to 10 minutes which time is sufficient for substantial completion of said alkylation and insufficient for appreciable isomerization of said para alkyl phenol; quenching the resulting alkylation reaction mixture and producing an aqueous phase containing said catalyst and an organic phase containing said para alkyl phenol by introducing water into said mixture; and recovering said alkyl phenol from said organic phase.

2. The improved process according to claim 1 wherein said olefin is polypropylene tetramer.

3. The improved process according to claim 1 wherein the phenol to olefin mol ratio is in the range of from about 5:1 to 1:1.